United States Patent
Förster

(10) Patent No.: US 6,832,911 B2
(45) Date of Patent: Dec. 21, 2004

(54) DEVICE FOR RELOCATING A LOWER JAW RELATIVE TO AN UPPER JAW

(76) Inventor: Rolf Förster, Vogesenallee 58, 75173 Pforzheim (DE)

( * ) Notice: Subject to any disclaimer, the term of this patent is extended or adjusted under 35 U.S.C. 154(b) by 0 days.

(21) Appl. No.: 10/427,110

(22) Filed: Apr. 30, 2003

(65) Prior Publication Data

US 2003/0207226 A1 Nov. 6, 2003

(30) Foreign Application Priority Data

| May 3, 2002 | (DE) | ......................................... 102 21 027 |
| May 25, 2002 | (DE) | ......................................... 102 23 381 |
| Jun. 13, 2002 | (DE) | ......................................... 102 26 240 |

(51) Int. Cl.$^7$ ................................................. A61C 7/00
(52) U.S. Cl. ...................................................... 433/19
(58) Field of Search .............................. 433/19, 18, 7, 433/21, 5

(56) References Cited

U.S. PATENT DOCUMENTS

| 3,798,773 A | * | 3/1974 | Northcutt ..................... 433/19 |
| 4,144,643 A | * | 3/1979 | Krygier ......................... 433/7 |
| 5,879,157 A | * | 3/1999 | Scheu ........................... 433/19 |
| 5,919,042 A | | 7/1999 | Williams |
| 6,036,488 A | | 3/2000 | Williams |
| 6,241,517 B1 | | 6/2001 | Williams |

OTHER PUBLICATIONS

U.S. 2002/0031741 A1; Publication Date: Mar. 14, 2002; Patentee: Williams; Filing Date: Dec. 29, 2000.

* cited by examiner

*Primary Examiner*—Melba Bumgarner

(57) ABSTRACT

A device for relocating a lower jaw relative to an upper jaw having a first sleeve with a first holder mounted on its one end, and a second sleeve. An internal thread is located in one of the two sleeves and a matching external thread on the other sleeve, by which they are screwed together over varying lengths. A third sleeve having one end, i.e. the end facing the first holder, is mounted on the second sleeve and is adapted to dampen impacts that may act in the longitudinal direction. A rod is arranged in the third sleeve for longitudinal displacement. A second holder is mounted outside the third sleeve on that end of the rod which faces away from the first holder. A stop is provided on the rod or in the neighborhood of the second holder, and abuts directly or indirectly against that end of the third sleeve which faces away from the first holder and toward the second holder. The length of the rod is selected to ensure that in its abutting position it will extend right into the first sleeve.

22 Claims, 6 Drawing Sheets

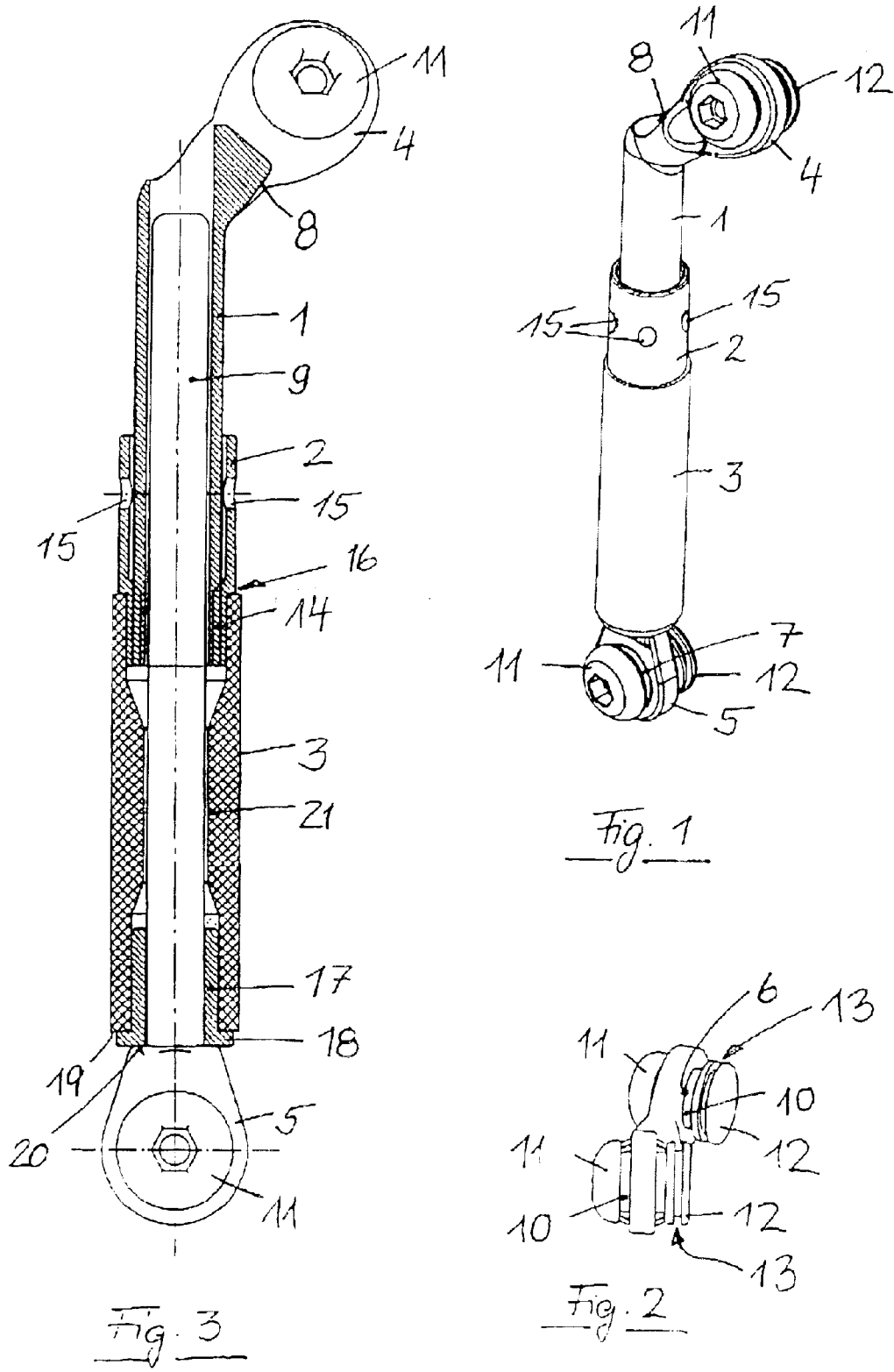

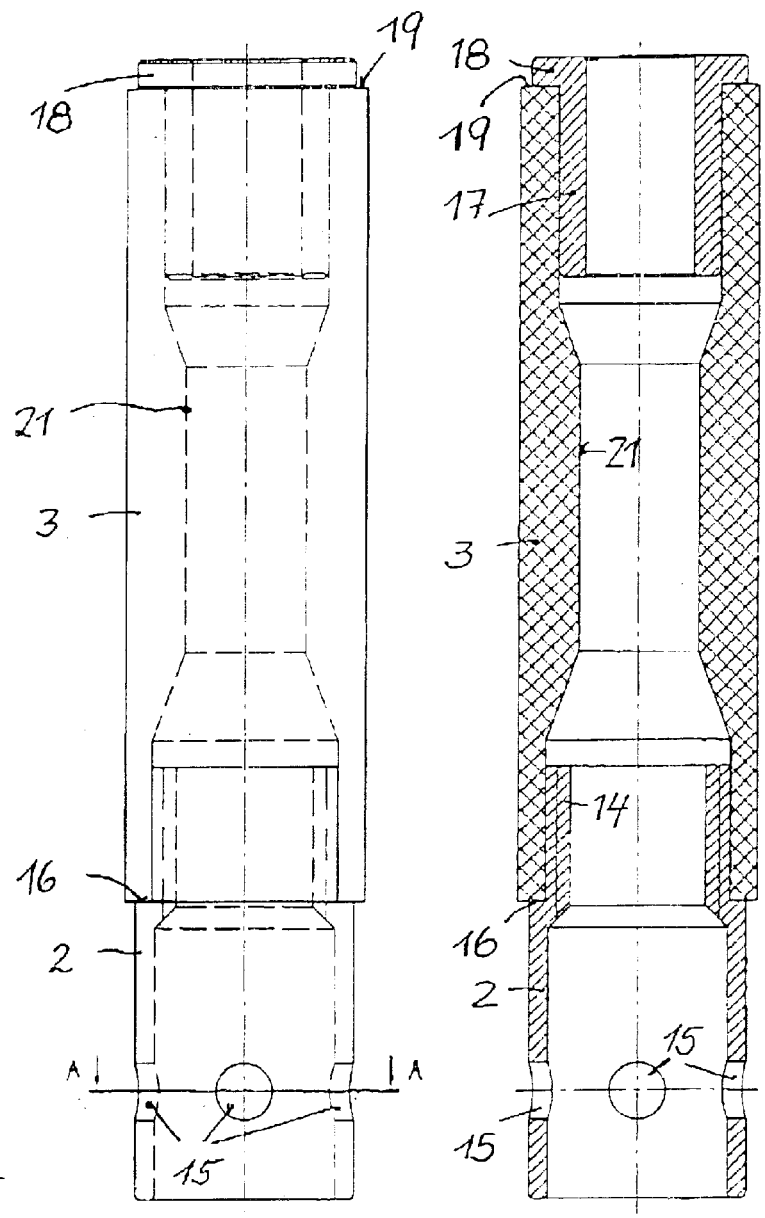
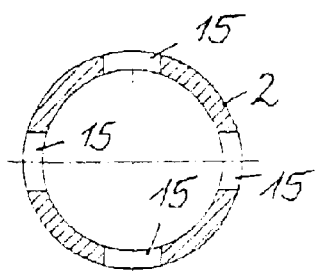
Fig. 4
Fig. 6
Fig. 5

DEVICE FOR RELOCATING A LOWER JAW RELATIVE TO AN UPPER JAW

The present invention relates to a device for relocating a lower jaw relative to an upper jaw, especially according to the principle of a Herbst hinge. A device of that kind described by U.S. Pat. No. 5,919,042 comprises a first sleeve having a first holder mounted on its one end and an external thread provided on its other end, a second sleeve provided with a matching internal thread so that the first sleeve can be screwed into the second sleeve over different lengths, and a rod arranged in the two sleeves for longitudinal movement and provided with a second holder on its end facing away from the first holder. The two holders are configured as eyes by means of which the device can be mounted in articulated fashion on the one hand on a molar strip in the upper jaw and, on the other hand, on a molar strip in the lower jaw. The device can follow the movements of the lower jaw, when the patient chews or opens or closes his mouth, by the rod moving back and forth in the two sleeves. When the patient bites his teeth together, the holder of the rod abuts against the second sleeve, and thereafter the lower jaw is necessarily displaced relative to the other jaw as the biting action continues. That change occurs abruptly, and considering the high forces that may be applied by the strong muscles of the jaw it may be felt as unpleasant or—in some cases—even painful and may lead to damage to the teeth and to the device as such.

Now, it is the object of the present invention to overcome these disadvantages by an improved structure of the device.

The invention achieves that object by a device having the features defined in claim 1. Advantageous further developments of the invention are the subject-matter of the sub-claims.

The device according to the invention comprises three sleeves which interact with a rod in the way of a telescope. One end of the first sleeve carries a first holder. The first sleeve and the second sleeve are screwed together, for which purpose one of the sleeves is provided with an internal thread, the other one with a matching external thread. This permits the one sleeve to be screwed into the other sleeve a longer or shorter length, so as to vary the effective length of the device. One end of the third sleeve, i e. the end facing the first holder, is mounted on the second sleeve and adapted to dampen impacts that may act in the longitudinal direction. The rod is arranged in the third sleeve for longitudinal displacement and comprises a second holder, which is mounted outside the third sleeve on that end of the rod which faces away from the first holder. A stop provided on the rod in the neighborhood of the second holder, or on the second holder, abuts directly or indirectly against that end of the third sleeve which faces away from the first holder and toward the second holder. The length of the rod is selected to ensure that in its abutting position it will extend right into the first sleeve. The two holders serve to mount the device in articulated fashion on the patient's upper jaw and lower jaw, usually on the molars of the upper jaw and the lower jaw, and those molars may be enclosed for this purpose by molar strips carrying counter-holders that coact with the respective holder of the device.

When the patient bites his teeth together, the rod then no longer abuts against the second sleeve, but rather against the third sleeve, which dampens the impact produced by the biting action. Accordingly, the device according to the invention is much more comfortable for the patient than known devices and does not cause any pain or damage when the patient bites his teeth together, neither on the teeth nor on the device as such, which furthers the patient's willingness to wear the device and thereby accelerates the orthodontic correction of the position of the teeth intended to be achieved by the device. That effect is further strengthened by the fact that the length of the device can be increased as the correction process progresses by turning the second sleeve relative to the first sleeve without any need to remove the device from the mouth, whereby the orthodontic treatment is further accelerated, and its cost is reduced.

Conveniently, the external thread is provided on the first sleeve, namely on that end of the first sleeve which faces away from the first holder, while the internal thread is arranged on the second sleeve, likewise on that end which faces away from the first holder. If the degree of adjustability is sufficient, the second sleeve can then stabilize the sleeve and does not have to extend into the third sleeve for damping purposes, except for its threaded portion.

Preferably, the third sleeve consists entirely or in part of an elastomeric material, especially a silicon plastic material, which on the one hand offers sufficient damping properties and, on the other hand, is especially suited for use in the bacterial and electrolytically not neutral environment of the mouth. The third sleeve may, however, also consist of a combination of a rigid portion and a dampening portion. Likewise, a corrugated tube could be used for the third sleeve. One advantage of the invention is seen in the fact that it is possible, by suitable selection of the material used and of the configuration of the third sleeve, to select at desire not only the dampening efficiency, but also the dampening characteristic. The dampening characteristic may be linear, which means that after compression the resistive force decreases linearly as the third sleeve is restored to its original length; such a characteristic can be achieved, for example, with the aid of a corrugated tube. Preferably, a progressive dampening characteristic is selected, which means that after compression the third sleeve is restored to its original length superproportionally as the compressive force is relieved.

The stop of the rod may abut directly against the end of the third sleeve when the patient bites his teeth together. Especially when the third sleeve consists of an elastomeric material, entirely or in part, it is, however, advantageous if a rigid bush, especially a metallic bush that guides the rod and against which a stop of the rod can abut is fitted in that end of the third sleeve which faces away from the first holder. The bush is preferably provided for that purpose with a collar that is in contact with the end face of the third sleeve that faces away from the first holder. Such a bush may be fixed in the third sleeve by pressing, bonding or in any other way. The bush may serve not only as a stop for transmitting the forces produced during the biting action to the dampening elastomeric sleeve, but at the same as a means for guiding the rod in the longitudinal direction so that the rod is guided not only in the first and the second, but also in the third sleeve. In order to further improve the guiding effect, the third sleeve preferably contains a central portion whose inner diameter is smaller than the inner diameter of the end portion of the third sleeve by an amount which guarantees that the rod can be guided in the longitudinal direction also in the central portion of the third sleeve, in the area between the bush and the end portion of the third sleeve connected with the second sleeve. The rod then simultaneously stabilizes the elastomeric sleeve when the latter is compressed by the biting action. The rigid, preferably metallic elements of the device, namely the first sleeve, the second sleeve, the rod and the bush then coact with the dampening, especially elastomeric sleeve in a meaningful way so that on the one hand stable relocation of the lower jaw relative to the upper jaw is achieved while on the other hand the forces that occur abruptly when the patient bites his teeth together are dampened to a comfortable and well-tolerated degree.

In the third portion of the third sleeve, and in the third sleeve, the rod is guided preferably with somewhat greater play than in the bush of the third sleeve, whereby an optimum of reliable guidance on the one hand and easy movement on the other hand is achieved.

In order to permit the length of the device to be adjusted in the mouth, without any need to remove it from the mouth, the second sleeve is preferably provided with means in which a wrench can be positively engaged for turning the second sleeve. These means may consist of flat portions on the outside of the second sleeve, on which a fork wrench can be fitted, or of radial bores in the second sleeve in which a pin can be engaged for turning the second sleeve.

The device according to the invention uses conveniently ahead screw with a recess defined by surfaces, the cross-section of which defines a regular polygon in which a matching socket wrench can be engaged. At least one of the surfaces defining the recess should enclose with the longitudinal axis of the head screw an outwardly opening small angle different from 0°. That further development of the invention will be described hereafter with reference to a head screw where the recess has the form of an internal hexagon in which a matching hexagon socket wrench can be engaged. The embodiment using the hexagon is preferred. Other embodiments, especially such using a square or a triangular shape are likewise suited.

A recess of that kind tapers from the outside to the inside. A conventional two-legged bent-off hexagon socket wrench, which is defined by surfaces extending in parallel to the longitudinal axis of its legs, is inserted into the narrowing internal hexagon of the head screw until it is eventually wedged, whereby the head screw is secured against slipping off the hexagon socket wrench unintentionally. Once the thread of the head screw grips in the internal thread of the counter-holder, the socket wrench can be withdrawn from the head screw and can be inserted once more in the hexagonal recess in a different angular position to continue the screwing-in operation.

Another advantageous embodiment uses a head screw whose head is provided with a recess in the form of a conventional internal hexagon defined by axially parallel surfaces. For turning that head screw, a likewise bent-off two-legged hexagon socket wrench, having a shorter and a longer leg, is used. In the case of that wrench, however, the outer hexagon of the shorter and/or the longer leg is defined by surfaces which enclose, with the longitudinal axis of the shorter or the longer leg, a small angle different from 0° so that the respective leg tapers towards its tip. In this case, too, the socket wrench is inserted into the recess of the head until it is wedged therein.

In principle, it is sufficient if only one of the surfaces that surround the recess in the head of the screw, only one of the surfaces that define the area of engagement of the socket wrench, encloses with the longitudinal axis of the head screw or with the longitudinal axis of the respective leg of the socket wrench, respectively, an angle different from 0°. In that case, the best wedging effect is achieved by an angle of 2° to 6°, especially 4°. The same applies by analogy if more than one surfaces are inclined relative to the respective longitudinal axis at an angle different from 0°, provided the respective opposite surfaces extend in parallel to the respective longitudinal axis.

Preferably, only two mutually opposite surfaces enclose with the respective longitudinal axis an angle different from 0°:

In that case, the best wedging effect is achieved if the angle, measured relative to the longitudinal axis, is equal to between 1° to 3°, preferably 2°, which corresponds to a total opening angle of the two inclined surfaces of between 2° to 6°, preferably 4°. If more than one pair of opposite surfaces, or all surfaces, are inclined relative to the respective longitudinal axis, the same applies by analogy.

Two exemplary embodiments of the invention are illustrated in the attached drawings in which:

FIG. 1 shows an oblique view of a device according to the invention;

FIG. 2 shows the same device, viewed from its one end;

FIG. 3 shows a lengthwise section through the same device;

FIG. 4 shows a detail, namely a side view of the second and the third sleeve of the device;

FIG. 5 shows a lengthwise section through the arrangement of FIG. 4;

FIG. 6 shows a section taken along line A—A in FIG. 4 through the second sleeve.

Figure 7:
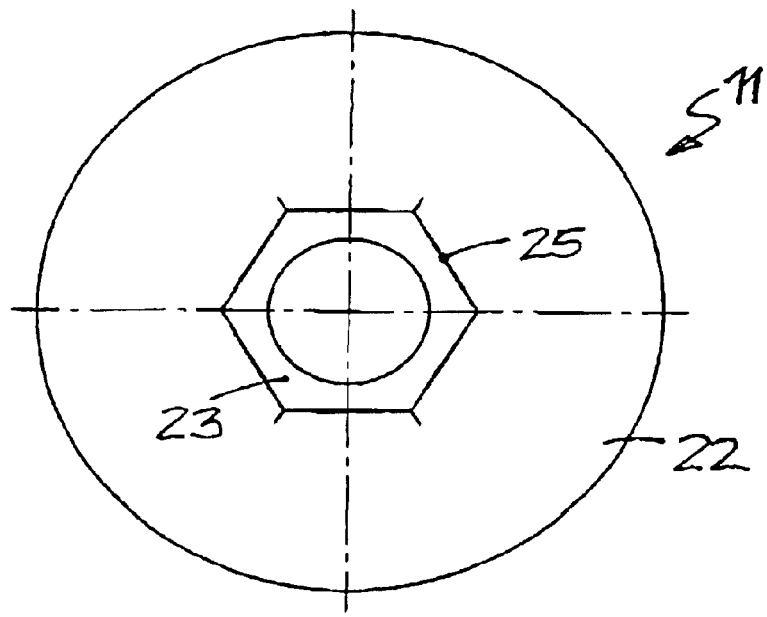
FIG. 7 shows a detail, namely a top view of the head of a head screw used in the device.

The device illustrated comprises a thinner first sleeve 1 screwed into a thicker sleeve 2. Mounted on the second sleeve 2 is a third sleeve 3, made from a plastic material of a kind which is capable of dampening impacts, especially from an elastomeric plastic material. In order to allow the device to be mounted in a patient's mouth on the upper jaw and on the lower jaw, a first holder in the form of an eye 6 is provided at the end of a short arm 8, which is mounted on one end of the first sleeve 1 and which extends at an obtuse angle relative to the first sleeve 1. A second holder 7, comprising a further eye 7, is mounted on a rod 9 that extends through the third sleeve 3 and into the first sleeve 1. Nuts 10 with a cylindrical shaft are fitted in each of the eyes 6 and 7 in such a way that they can be turned in the eye 6 or 7, respectively. A screw 11 can be screwed into the nut from the one end. At the other end of the nut, there is provided a mounting element 12 by means of which the nut can be fixed on a counter-holder, for example a molar strip, for example by welding or soldering, or by means of which it can be embedded in a plastic holder, for which purpose it comprises an angular groove 13. The plastic holder as such, which is not an element of the present invention, can be fixed on a dental arch in the patient's mouth, an operation which is known to any man skilled in the art.

In order to connect the first sleeve 1 and the second sleeve by screwing, the first sleeve 1 is provided, on its end facing away from the first holder 4, with an external thread by means of which it is screwed into a matching inner thread 14 of the second sleeve 2. The internal thread 14 is likewise provided on the end of the second sleeve 2 opposite the first holder 4. The second sleeve 2 comprises four radial bores 15 that are distributed over the circumference of the second sleeve 2 at respective angles of 90°. By inserting a pin into such a bore 15 it is possible to rotate the second sleeve 2 relative to the first sleeve 1 in order to vary the device.

In the area of the internal thread 14, the outer diameter of the second sleeve 2 is reduced, forming a shoulder 16, and an end portion of the third sleeve 3 is fitted and fixed on that reduced portion, for example by bonding or shrinking. A bush 17, provided with a collar 18, is introduced into the third sleeve 3 from the other end until its collar 18 gets into contact with the end face 19 of the third sleeve. The bush 17 serves on the one hand for guiding the rod 9 in precisely fitting fashion, and on the other hand for transmitting any forces, that may suddenly occur when the patient bites his teeth together, to the third damping sleeve 3. This is so because, when the patient bites his teeth together, the rod 9 is pushed into the sleeves 1 to 3 until a stop 20, provided on the second holder 5, comes to abut against the collar 18 This impact is dampened by the third sleeve 3 to such an extent that it will not have any detrimental effects on the teeth and on the device as such, via the holders 4 and 5

Figure 12:
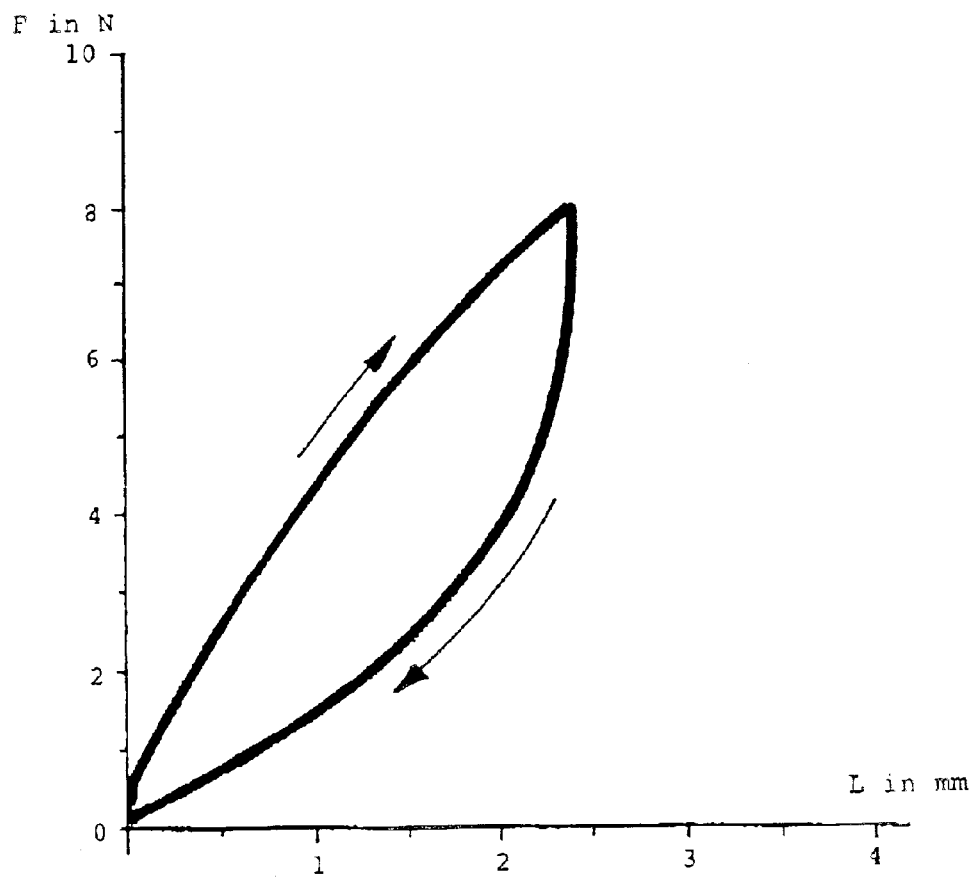
FIG. 12 shows a typical dampening characteristic of an elastomeric sleeve.

The inner clearance of the central portion 21 of the third sleeve 3, with its cylindrical outside, is so narrow that that portion contributes, just as the first sleeve 1, toward guiding the rod 9 although, compared with the bush 17, a little more play is allowed for the rod 9 in order to ensure easy moving conditions. Due to its special configuration, with a thicker central portion 21 and thinner end portions, the third sleeve 3 exhibits a desirable progressive damping behavior in combination with an efficient guiding effect for the rod 9. A corresponding typical characteristic is illustrated in FIG. 12. It shows the interdependence between pressure and compression of the third sleeve. When pressure is applied to the ends of the sleeve 3, its length is initially reduced in approximately linear fashion. When the pressure is relieved, the length is restored progressively, i.e. in superproportional fashion. This finds its expression in a hysteresis loop of the characteristic. The surface enclosed by the hysteresis loop provides a measure for the damping effect.

Figure 9:
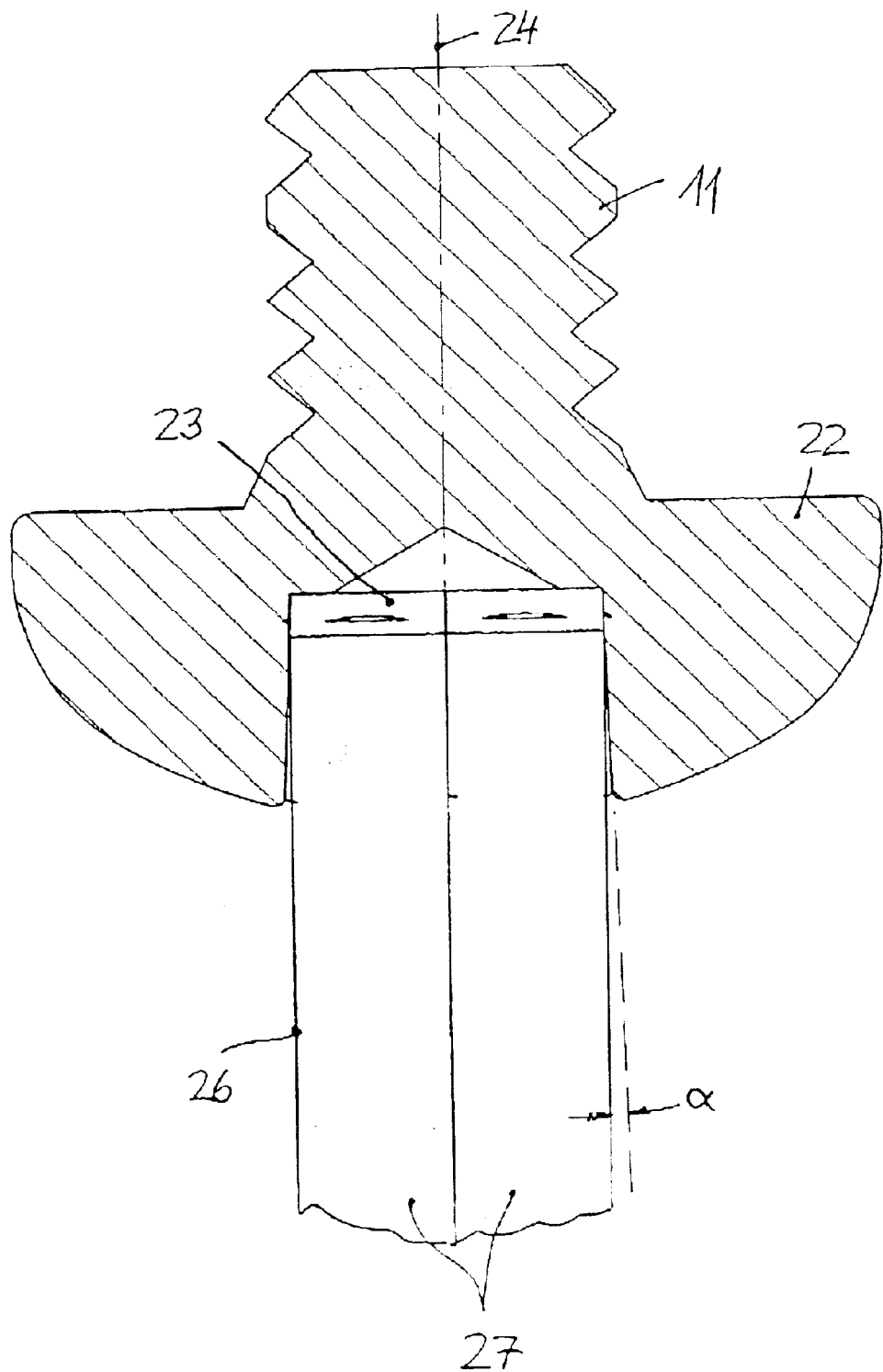
FIG. 9 shows a lengthwise section through the head screw of FIG. 8, with fitted hexagon socket wrench.

The head screw 11 comprises a head 22 with a recess 23 in the form of an internal hexagon defined by six surfaces 25, that extend at a small angle of 2° relative to the longitudinal axis 24 of the head screw 11. A conventional bent-off hexagon socket wrench 26, whose six surfaces 27, forming the outer hexagon, extend in parallel to its longitudinal axis 28, are wedged during insertion into the recess 23 before it reaches the end of the recess 23, as illustrated in FIG. 9. As a result of that wedging effect, the head screw 11 can be guided to the nut 10 and can be turned in the patient's mouth without getting lost.

Figure 8:
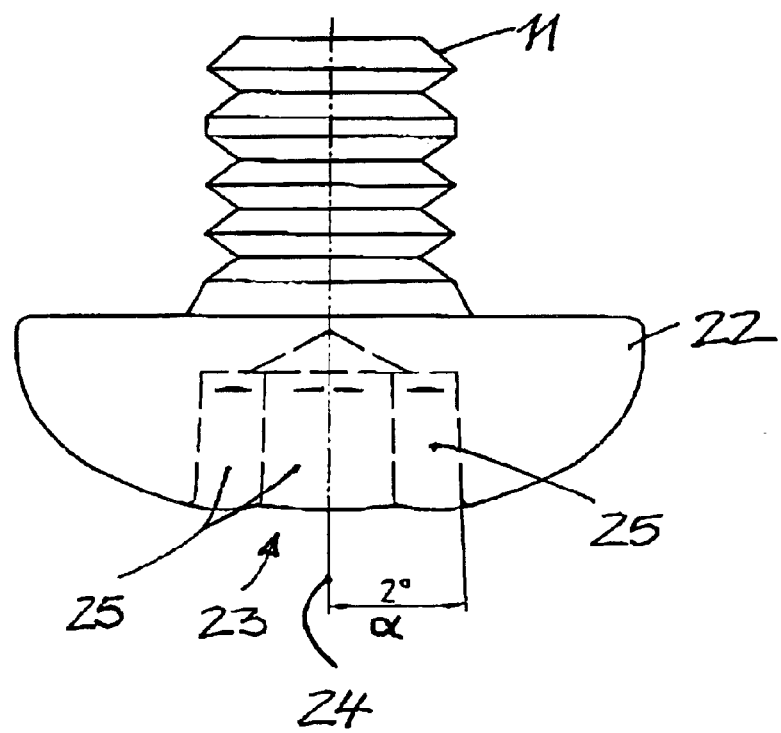
FIG. 8 shows a side view of the head screw of FIG. 7.
Figure 10:
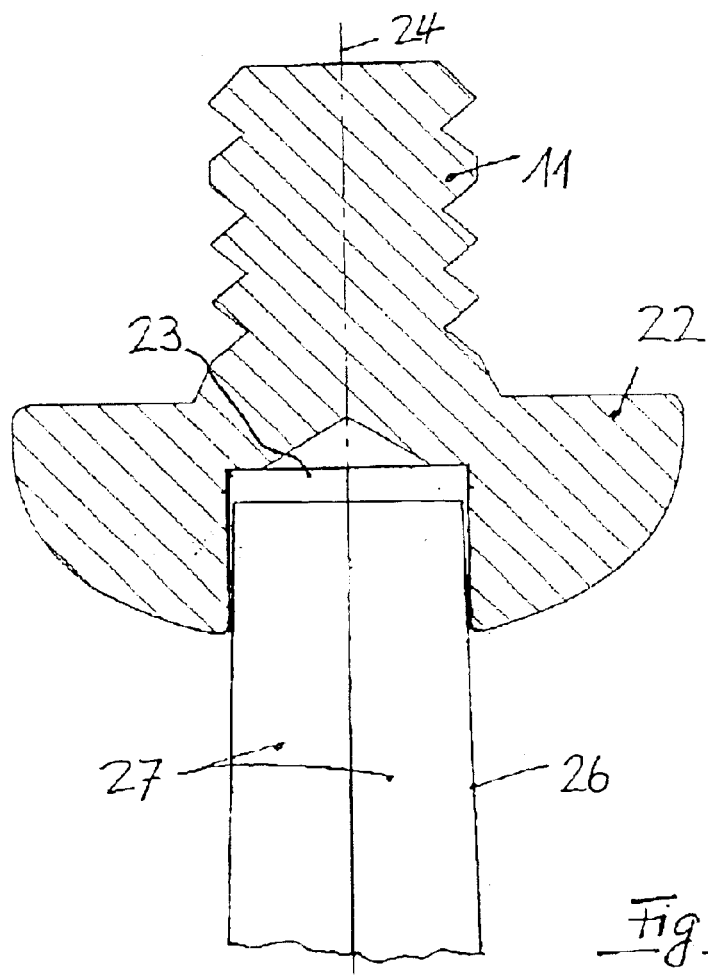
FIG. 10 shows a view similar to that of FIG. 9, but of a modified embodiment.
Figure 11:
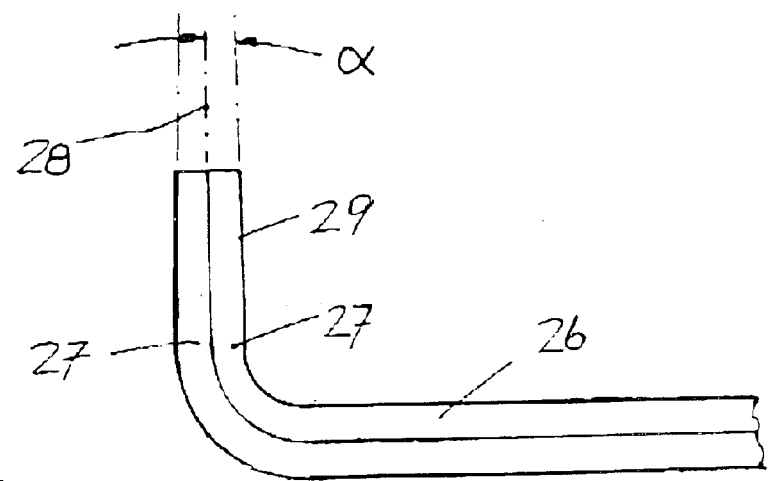
FIG. 11 shows a bent-off hexagon socket wrench as used in the second embodiment.

The other embodiment of the invention illustrated in FIGS. 10 and 11 differs from the embodiment illustrated in FIGS. 7 to 9 only in that the recess 23 in the head 22 is defined by surfaces 25 that extend in parallel to the longitudinal axis 24 of the head screw. The tool used for the head screw 11 consists in that case of a bent-off hexagon socket wrench 26 which is defined on a shorter leg 29 by six surfaces 27 that taper toward the tip of the shorter leg 29 at an angle of 2° relative to its longitudinal axis 28. The wedging effect occurs in this case in the area of the outer edge of the recess 23, between the socket wrench 26 and the head screw 11.

What is claimed is:

1. A device for relocating a lower jaw relative to an upper jaw, the device comprising:
   a first sleeve with a first holder mounted on its one end;
   a second sleeve having an internal thread in one of the two sleeves and a matching external thread on the other sleeve, by means of which they are screwed together over a variable length;
   a third sleeve having an end facing the first holder mounted on the second sleeve
   a rod arranged in the third sleeve for longitudinal displacement;
   a second holder, which is mounted outside the third sleeve on an end of the rod which faces away from the first holder; and
   a stop provided on the rod, on or in the neighborhood of the second holder, and abutting directly or indirectly against the end of the third sleeve which faces away from the first holder and toward the second holder, a length of the rod being selected to ensure that in an abutting position the rod will extend into the first sleeve; said third sleeve being adapted to dampen impacts that act in a longitudinal direction, by compression of the third sleeve between said ends, as the rod moves within said third sleeve.

2. The device as defined in claim 1, wherein the external thread is provided on the first sleeve and the internal thread on the second sleeve.

3. The device as defined in claim 1 or claim 2, wherein the external thread is provided on the end of the first sleeve which faces away from the first holder.

4. The device as defined in claim 1, wherein the third sleeve consists of an elastomeric material, entirely or in part.

5. The device as defined in claim 4, wherein the elastomeric material is a plastic material.

6. The device as defined in claim 4, wherein the elastomeric material is a silicon plastic material.

7. The device as defined in claim 1, wherein a bush that guides the rod and against which the stop of the rod can abut, is fitted in that the end of the third sleeve which faces away from the first holder.

8. The device as defined in claim 7, wherein the bush is provided with a collar which is in contact with the end face of the third sleeve, which faces away from the first holder.

9. The device as defined in claim 7 wherein the play existing between the central portion of the third sleeve and the rod is greater than that between the bush and the rod.

10. The device as defined claim 7 wherein the play existing between a first sleeve and the rod is greater than that between the bush and the rod.

11. The device as defined in claim 1, wherein the third sleeve comprises a central portion with an inner diameter smaller than the inner diameter of the end portions of the third sleeve.

12. The device as defined in claim 11, wherein the inner diameter of the central portion of the third sleeve is equal to the inner diameter of the first sleeve.

13. the device as defined in claim 1, wherein the structure of the third sleeve is such that it exhibits a progressive damping characteristic.

14. The device as defined in claim 1, wherein the second sleeve comprises means which can be positively engaged by a wrench for turning the second sleeve.

15. The device as defined in claim 1, wherein the holders are provided with an eye through which the device can be mounted by means of a head screw on a counter-holder, said counter-holder being provided for this purpose with an internal thread matching the thread of the head screw, the head screw comprising, for engagement with a socket wrench whose contour in the socket area is configured in the form of a regular polygon, a matching recess whose cross-section likewise exhibits the shape of a regular polygon, and at least one of the surfaces defining the recess encloses with the longitudinal axis of the head screw a small angle (a) different from 0° that opens toward the outside.

16. The device as defined in claim 1, wherein the holders are provided with an eye through which the device can be mounted by means of a head screw on a counter-holder, said counter-holder being is provided for this purpose with an internal thread matching the thread of the head screw, in combination with a bent-off socket wrench having two differently long legs and, in the socket area, a contour configured in the form of a regular polygon, with the head of the head screw comprising, for engagement by that socket area, a matching recess whose cross-section likewise exhibits the shape of a regular polygon and is defined by axially parallel surfaces, and that at least one of the surfaces defining the socket area of the shorter and/or the longer leg of the socket wrench encloses with its longitudinal axis a small angle (a) different from 0° so that the respective leg tapers toward its tip.

17. The device as defined in claim 15 or claim 16, wherein the polygon is a hexagon.

18. The device as defined in claim 15 or 16, wherein there are two oppositely arranged surfaces and the angle (a) different from 0° is enclosed between each of said two oppositely arranged surfaces and the respective, longitudinal axis.

19. The device as defined in claim 18, wherein the angle (a) is 1° to 3°.

20. The device as defined in claim 18, wherein the angle (a) is 2°.

21. The device as defined in claim 15 or 16, wherein the at least on at in the case where the surfaces, which enclose with the respective longitudinal axis a small angle (a) different from 0°, is arranged opposite to surfaces which extend in parallel to the longitudinal axis and the angle (a) is 2° to 6°.

22. The device as defined in claim 21 wherein the angle (a) is 4°.

* * * * *